US010172788B2

(12) United States Patent
Colle et al.

(10) Patent No.: US 10,172,788 B2
(45) Date of Patent: Jan. 8, 2019

(54) CHEWING GUMS

(71) Applicant: Perfetti Van Melle S.P.A., Lainate (Milan) (IT)

(72) Inventors: Roberto Colle, Lainate (IT); Andrea Sarrica, Lainate (IT); Maurizio Deleo, Lainate (IT)

(73) Assignee: PERFETTI VAN MELLE S.P.A., Lainate (MI) (IT)

( * ) Notice: Subject to any disclaimer, the term of this patent is extended or adjusted under 35 U.S.C. 154(b) by 0 days.

(21) Appl. No.: 15/421,509

(22) Filed: Feb. 1, 2017

(65) Prior Publication Data
US 2017/0143620 A1 May 25, 2017

Related U.S. Application Data

(60) Continuation of application No. 15/089,646, filed on Apr. 4, 2016, now abandoned, which is a division of application No. 14/431,880, filed as application No. PCT/IB2013/059341 on Oct. 14, 2013, now abandoned.

(30) Foreign Application Priority Data

Oct. 15, 2012 (IT) .............................. MI2012A1734

(51) Int. Cl.
| *A61K 9/68* | (2006.01) |
| *A23G 4/06* | (2006.01) |
| *A23G 4/12* | (2006.01) |
| *A23G 4/20* | (2006.01) |
| *A61K 31/05* | (2006.01) |
| *A61K 31/353* | (2006.01) |
| *A61K 33/30* | (2006.01) |
| *A61K 36/575* | (2006.01) |
| *A61K 36/82* | (2006.01) |
| *A61K 8/97* | (2017.01) |
| *A61Q 11/00* | (2006.01) |
| *A61K 8/27* | (2006.01) |
| *A61K 8/02* | (2006.01) |
| *A61K 45/06* | (2006.01) |
| *A61K 47/26* | (2006.01) |

(52) U.S. Cl.
CPC ................ *A61K 8/97* (2013.01); *A23G 4/064* (2013.01); *A23G 4/068* (2013.01); *A23G 4/12* (2013.01); *A23G 4/20* (2013.01); *A61K 8/02* (2013.01); *A61K 8/27* (2013.01); *A61K 9/0058* (2013.01); *A61K 31/05* (2013.01); *A61K 31/353* (2013.01); *A61K 33/30* (2013.01); *A61K 36/575* (2013.01); *A61K 36/82* (2013.01); *A61K 45/06* (2013.01); *A61K 47/26* (2013.01); *A61Q 11/00* (2013.01); *A23V 2002/00* (2013.01); *A61K 2800/244* (2013.01); *A61K 2800/92* (2013.01)

(58) Field of Classification Search
CPC .......... A23G 4/20; A23G 4/064; A23G 4/068; A23G 4/12; A61K 33/30; A61K 9/0058; A61K 36/82; A61K 8/97; A61K 8/27; A61K 31/05; A61K 31/353; A61Q 11/00; A23V 2002/00
See application file for complete search history.

(56) References Cited

U.S. PATENT DOCUMENTS

| 2003/0049303 A1* | 3/2003 | Ning ........................ A23G 3/36 424/439 |
| 2008/0131379 A1* | 6/2008 | Kristiansen ............ A23G 4/043 424/48 |

FOREIGN PATENT DOCUMENTS

| KR | 20040019145 A | 3/2004 |
| WO | 2006079343 A1 | 8/2006 |
| WO | 2007067340 A1 | 6/2007 |

OTHER PUBLICATIONS

International Preliminary Report on Patentability of PCT/IB2013/059341 dated Oct. 28, 2014.
International Search Report and Written Opinion of PCT/IB2013/059341 dated Feb. 5, 2014.
Porciani et al., "The effect of zinc acetate and magnolia bark extract added to chewing gum on volatile sulfur-containing compounds in the oral cavity", The Journal of Clinical Dentistry, 2012, vol. 23, No. 3, Jul. 1, 2012, pp. 76-79.

* cited by examiner

*Primary Examiner* — Doan T Phan
(74) *Attorney, Agent, or Firm* — Silvia Salvadori, P.C.; Silvia Salvadori

(57) ABSTRACT

The present invention relates to chewing gum containing a synergic combination of zinc and vegetable extracts containing polyphenols.
Said chewing gum is useful in treating the symptoms of halitosis.

15 Claims, No Drawings

CHEWING GUMS

This Non-Provisional Application is a Continuation of U.S. Ser. No. 15/089,646 filed on Apr. 4, 2016, which is a Divisional Application of U.S. Ser. No. 14/431,880 filed on Mar. 27, 2015, which is a National Stage of PCT/IB2013/059341 filed on 14 Oct. 2013, which claims priority to and the benefit of Italian Application No. MI2012A001734 filed on 15 Oct. 2012, the contents of which are incorporated herein by reference in their entirety.

The present invention relates to chewing gums.

PRIOR ART

Halitosis is a condition that restricts the sufferer's social life. It is estimated that 15% to 40% of the population suffers from moderate halitosis (Rosing C K et al., Braz Oral Res 2011; 25(5):466-71). Bad breath is usually caused by the presence of volatile sulphur compounds (VSC) (Kleinberg I et al., Crit Rev Oral Biol. Med. 1990; 1(4):247-59). Said compounds are generated by catabolism of proteins by the oral bacteria (De Boever E H et al., J Am. Dent. Assoc 1995; 126(10):1384-93). The nose can perceive very low concentrations of VSC as an unpleasant odour; in clinical practice it is considered that 75 ppb (parts per billion) of VSC in the air exhaled is the minimum threshold for a classification of moderate halitosis (van den Broek A M. et al., J Dent. 2007; 35:627-635).

Some foods, such as garlic and Brussels sprouts, can increase halitosis (Tangerman A. Halitosis in medicine: a review. *Int. Dent J.* 2002; 52 Suppl. 3:201-206). Moreover, "morning breath" may be present at the beginning of the day, mainly caused by stagnation of the saliva produced during the night (Rosenberg M. J. Am. Dent. Assoc. 1996; 127: 475-482). Most research and patented inventions concentrate on antibacterial treatment of the causes of halitosis at particular times of day (morning) or after eating particular foods (such as mouthwashes based on garlic or methionine).

Vegetable extracts are used and described due to some properties against halitosis; for example, coated products in the form of corrugated sugar-free pastilles containing vegetable extracts can be found on the market (Hali Control™ containing 0.36% green coffee beans and 0.36% burdock).

Sweets and chewing gum containing green tea extracts are known to reduce halitosis generated by garlic-based mouthwashes (H. Yasuda, et al., Nippon Shishubyo Gakkai Kaishi, 37, 141, 1995). Chewing gum and tablets containing *magnolia* bark extract (MBE) are also known to reduce the salivary concentration of some bacteria, considered to be among the causes of halitosis (Greenberg M et al., J. Agric. Food Chem. 2007; 55(23):9465-9). However, chewing gums for use against the symptoms of halitosis, which are not generated artificially and use synergic formulations of said vegetable extracts with zinc salts, are not known.

An article has been published about the ability of mouthwashes based on zinc salts to reduce the volatile sulphur compounds generated artificially after rinsing the mouth with cysteine, an aminoacid containing sulphur. In said article, the effective amount of zinc (administered as zinc acetate dihydrate) ranged from a minimum of 3 mg to a maximum of 30 mg (Young, A et al., (2003). Eur. J. Oral Sci. 111(5): 400-404).

One study of chewable tablets containing 6.8 mg of Zn, in the form of various salts, concluded that the effect against VSC, generated artificially by a cysteine mouthwash, is independent of the solubility constants of the salts (Young, A., G. Jonski et al. (2002), Eur. J. Oral Sci. 110(1): 31-34).

Finally, an in vivo study conducted on 11 volunteers found that chewing gum containing 2 mg or 0.5 mg of zinc acetate reduced VSC by 45% and 16% respectively, as against a 14% reduction after chewing a placebo chewing gum. In practice, when 0.5 mg of zinc was used, the effect was indistinguishable from that of the placebo (Waler S M. Acta Odontol. Scand. 1997; 55(3):198-200).

Combinations of zinc or vegetable extracts with other ingredients, with an anti-halitosis function, have been illustrated in some patents. They involve incorporating the mixtures into chewing gum.

EP1998736 discloses combinations of *magnolia* bark extract and essential oils with an antibacterial function.

EP2046274 discloses combinations of *magnolia* bark extract and some flavouring compounds (in particular menthone and isomenthone) naturally contained in essential oils. Said combinations are said to be particularly effective in reducing halitosis caused by the consumption of halitosis-causing foods.

EP1901704 and EP1957169 disclose combinations of *magnolia* bark extract and surfactants.

WO 02091848 discloses the use of herbal extracts, including green tea extracts and *magnolia* bark extracts, combined with other oral hygiene ingredients such as xylitol (anti-plaque) and zinc (anti-halitosis). However, the optimum amounts for simultaneous use of vegetable extracts and zinc are not illustrated. The two functional ingredients are treated separately. In fact, the purpose of the vegetable extracts is to combat halitosis, whereas the purpose of the other functional ingredients (oral care actives) is to provide further benefits in the oral hygiene area.

The herbal extracts are said to perform their action by means of an antibacterial effect, while an effect on VSC is not reported.

EP1387662 discloses the use of two different metal ions combined with polyphosphates, and optionally MBE. EP1843731 also discloses the use of MBE combined with polyphosphates, but with an anti-tartar function.

WO2006/079343 discloses gums in tablet form containing zinc salts and green tea extracts.

WO2007/067340 reports the use of *magnolia* extracts, and optionally zinc, in chewing gum.

KR2004/0019145 reports mouthwashes containing zinc salts and green tea. There are no teachings relating to synergic combinations of MBE and zinc in chewing gum, especially as regards the optimum doses able to guarantee long-lasting symptomatic treatment after a single use of the chewing gum by patients suffering from real halitosis, ie. halitosis not caused by mouthwashes containing sulphated amino acids or garlic, and not associated with specific times of day (morning).

DESCRIPTION OF THE INVENTION

It has now been found that it is possible to prepare a chewing gum consisting of at least one first region with gum base and a second, fully water-soluble region without gum base, comprising a synergic combination of an effective amount of vegetable extracts selected from *magnolia* bark extract, green tea extract and combinations thereof and an effective amount of zinc ions, at least partly contained in microgranules which are fully water-soluble.

The invention allows the use of lower amounts of zinc than is taught in the literature. This generates an organoleptic advantage, as zinc has a marked astringent power, which can improve compliance with the treatment, as well as providing an economic benefit.

The invention can be advantageously used to treat the symptoms of halitosis, namely to reduce the volatile sulphur compounds (VSC) in the exhaled air. In other words, a single portion of chewing gum, suitable to be consumed on one occasion, produces the above-mentioned effect.

"Single portion of chewing gum" means a single piece of chewing gum, or a number of pieces which can be consumed simultaneously. A single piece of chewing gum can be selected from the following formats and weights: a stick weighing 1 g to 3 g, a pellet weighing 1 g to 4 g, a pellet with filling weighing 1 g to 5 g, a bubble gum with liquid filling weighing 1 g to 9 g, or a multi-layer stick weighing 1.5 g to 9 g. A number of pieces which can be consumed simultaneously, to form a single portion, can be selected from the preceding formats; however, if a number of pieces combine to form a single portion, the weight of the single piece is preferably less than 3 g, even more preferably less than 2.5 g and, in some forms of embodiment, less than 1 g. In the embodiment according to the invention, the use of sugar-free chewing gum is particularly advantageous. The absence of fermentable sugars in the composition of the gum prevents the chewing gum from supplying fermentable substrates to micro-organisms connected with VSC production. At the same time, chewing increases the salivary flow which, through its cleansing action, produces a first effect of reducing VSC.

The chewing gum comprises flavours and additives such as sweeteners, acidifiers, thickeners, wetting agents, emulsifiers, antioxidants, stabilisers and coating agents.

In particular a chewing gum wherein said first region constitutes a core, and said second region, which is fully water-soluble, constitutes a coating that at least partly covers the first region, is preferable. Said forms are also known as pellets.

Chewing gum can made in various formats, such as cushion, ball, cube and disc shapes.

Methods of obtaining the first region of the chewing gum according to the invention, containing gum base, are known.

The ingredients of the first region of the chewing gum according to the invention, containing gum base, can be selected from gum base, sweeteners such as sugars, polyalcohols, intensive sweeteners, additives such as dyes, acidifiers, emulsifiers, flavours in solid or liquid form, wetting agents, technological adjuvants such as emulsifiers or plasticisers, active pharmacological ingredients, vegetable extracts, functional ingredients such as vitamins or mineral salts, and dyes.

If the form of embodiment according to the invention is a chewing gum in the form of a pellet, the first region is called the core, and the second region, which is fully water-soluble, is called the coating.

The two main types of coating are hard and soft coatings.

In hard coatings, the cores are inserted in a coating pan wherein, once in rotation, they undergo repeated syrup-spraying and drying cycles. Powders can be applied at some of these stages.

The syrups are constituted by mixtures of sugars or polyalcohols, water, binders, and optionally pigments, intensive sweeteners and flavours.

Polyalcohols are used to coat sugar-free chewing gum. The most commonly used polyalcohols include sorbitol, isomalt, maltitol and xylitol.

The preferred binders are hydrocolloids such as gum arabic, gelatin, starches, including modified starches, and mixtures thereof.

The powders can simply consist of polyols in crystals ground to very fine granulates, or mixtures of polyalcohols and binders, such as xylitol and gum arabic, mannitol and gum arabic, or maltitol and gum arabic.

The coating can constitute the second, fully water-soluble region. It is particularly advantageous to incorporate the vegetable extracts according to the invention in said second region. In other forms of embodiment, said second region does not consist of the coating, as illustrated below.

In some forms of embodiment, the vegetable extracts are contained in the first region of the chewing gum.

A coating consisting of maltitol or a mixture of glucopyranosyl-mannitol and glucopyranosyl-sorbitol amounting to more than 70% by dry weight of the coating is particularly advantageous.

In some forms of embodiment of the invention the first region can contain at least one filling, which may be a solid such as hard candy, toffee, chocolate, marzipan or fondant, or may consist of particulate matter containing xylitol or other polyalcohols in crystals, or dextrose in crystals. Alternatively, said filling can take the form of a fluid, such as a syrup. Combinations among the forms described by way of example are possible. The filling can contain one or more polyalcohols, additives, vitamins, mineral salts, including zinc salts, vegetable extracts, including green tea and *magnolia* bark extracts, dyes, acidifiers and flavours.

The filling is usually inserted in the first region, comprising gum base, during the extrusion stage.

Depending on the type of core and filling material, and on the shape of the piece of chewing gum, the filling can be totally incorporated in the piece of chewing gum or can be visible from the exterior of the chewing gum on one or more sides.

As an alternative to the pellet shape, the chewing gum according to the invention can be configured so that said first region and said second region are arranged in overlapping, alternating layers. Methods and formulations for said particular configuration are known (U.S. Pat. No. 5,437,879).

Regardless of the form of embodiment of the chewing gum according to the invention, the preferred flavours are those deriving from species of the genera *Mentha, Citrus, Spilanthes* and menthol, artificial and natural flavours with the function of refreshing and salivation-stimulating agents and combinations thereof. Flavours derived from various species of mint (peppermint, spearmint and the like) and citrus fruit (orange, lemon, grapefruit, lime and the like), artificial or natural flavours with the function of cooling agents, are associated with the sensation of cooling and cleanliness, and their pleasant odour can effectively mask the sensation of bad breath, thus completing the organoleptically perceptible effect of the reduction in the symptoms of halitosis.

Flavours with the function of cooling agents are typically menthol esters, such as menthyl lactate, menthyl succinate and menthyl glutarate; or amides such as N-ethyl-p-menthane-3-carboxamide, 2-isopropyl-N,2,3-trimethylbutyramide, ethyl 3-(p-menthane-3-carboxamido)-acetate, N-para-benzen-acetonitrile menthane carboxamide and N-(2-(pyridin-2-yl)ethyl)-3-para-menthane-3-carboxamide, but there may also be other compounds such as isopulegol and (−)-menthoxypropan-1,2-diol.

Flavouring compounds with salivation-stimulating properties such as spilanthol, to which other compounds with sialogogic properties such as pellitorine and sanshool have recently been added, are obtained from the genus *Spilanthes*.

Zinc is contained in the chewing gum in the form of ions. Hereafter, "zinc" therefore refers to the ionic form.

It is particularly advantageous to include zinc in the first region containing gum base. Inclusion in the zone with gum base results in slow release, which leads to long-lasting efficacy of the gum according to the invention.

The zinc is contained, at least partly, in fully water-soluble microgranules. The fully water-soluble microgranules do not contain polymers used in the manufacture of gum base. Preferably, the microgranules comprise one or more polyalcohols, hydrocolloids, flavours, dyes, sweeteners and other additives, either alone or mixed together. In a preferred form of embodiment the microgranules contain more than 80% sorbitol, less than 2% gum arabic and more than 1% zinc salt. "Microgranules" means a particulate matter, prepared before the manufacture of the gum, having a mean particle size of less than 1000 μm. In particular, a particle size such that at least 90% of the granules are between 800 μm and 300 μm is preferred. Although the microgranules can be introduced into the part with gum base or the fully water-soluble region, they are preferably contained in the region with gum base.

The synergic effect between vegetable extracts and zinc is more efficient when the content of zinc in ions ranges between 0.0005% and 0.05% by weight, and the vegetable extract ranges between 0.02% and 2% (percentages of finished product).

A single portion of chewing gum is particularly effective if it contains zinc ions ranging between 0.012 mg and 1.2 mg, and *magnolia* bark extract between 0.5 mg and 50 mg. As an alternative to *magnolia* extract, green tea extract can be used, either alone or mixed with *magnolia* bark extract.

The chewing gum according to the invention preferably consists of at least one region with gum base and one region without gum base, which is fully water-soluble. The region with gum base comprises zinc ions from 0.005% to 0.04% of the finished product, and the region without gum base contains *magnolia* bark extract ranging from 0.07% to 0.5% of the finished product.

The zinc can be wholly or partly carried by the microgranules previously described. Preferably at least 10%, and even more preferably at least 20% of the zinc is carried by the microgranules previously described, the rest being carried by salts directly included in the region with gum base.

In order for the zinc to be carried in the form of ions, the zinc ion is preferably present as salt selected from zinc chloride, acetate, lactate, gluconate, butyrate, glycerate, glycolate, formate, lactate, picolinate, propionate, salicylate, tartrate, sulphate, ascorbate, bisglycinate, lysinate, malate, mono-L-methionine sulphate, pidolate and mixtures thereof.

Zinc acetate, lactate and gluconate, and mixtures thereof, are particularly preferred.

It is preferable for the zinc ion to be present as salt selected from those characterized by water-solubility exceeding 0.5 g/100 g at 25° C. at a neutral pH. They are consequently water-soluble salts, which can be advantageously included in microgranules, while the microgranules can be included in the region with gum base.

In some embodiments of the invention the chewing gum contains an additional zinc salt selected from zinc oleate, stearate, citrate, phosphate, carbonate, borate, oxalate, aspartate, zinc oxide and mixtures thereof.

A single portion of chewing gum preferably contains said additional zinc salt in amounts that provide 0.1 to 10 mg of zinc.

In a preferred form of embodiment, the zinc salt inserted in the microgranules and the zinc salt not inserted in the microgranules are equal.

In an alternative form of embodiment, the zinc salt inserted in the microgranules is different from the zinc salt not inserted in the microgranules.

The chewing gums according to the invention reduce the oral content of volatile sulphur compounds more than a gum lacking said functional ingredients, and more than a gum containing only one of the two. The effect is greater both after chewing and over time, as will be demonstrated below.

*Magnolia* bark extract is particularly preferred.

*Magnolia* bark extract contains two neolignans, magnolol and honokiol, considered to be its active constituents. Analysis of traditional extracts originating from different regions of China demonstrates that the magnolol concentration ranges from a minimum of 0.005% to a maximum of 9.2%, while the honokiol concentration ranges from a minimum of 0.008% to a maximum of 9.7%. The sum of the two is always lower than 20% (Jiang, Y., et al., Phytochem. Anal, 2011, DOI 10.1002/pca.1369).

The two neolignans are extracted from bark prepared according to methods described (Pharmacopoeia of the PRC, (English edition), 1988, People's Medical Publishing House, Beijing, Cortex Magnoliae Officinalis, p 23-24). The extraction can be performed with organic solvents or, more recently, with supercritical carbon dioxide.

An extract obtained by extraction in supercritical carbon dioxide, followed by crystallisation in ethanol, is preferred.

An extract with a magnolol content ranging between 80% and 88%, and a honokiol content ranging between 8% and 18%, wherein the sum of the two neolignans is preferably greater than 85%, and even more preferably greater than 95%, is preferably used.

*Magnolia* bark extract can be obtained from various plants belonging to the genus *Magnolia*, including *Magnolia obovata* and *Magnolia officinalis*, and the bark can derive from the branches, trunk and roots of the plant. It is preferable to use extracts obtained from the sub-species *Magnolia officinalis Rehder* spp. *Biloba*. The extract is preferably obtained from trunk bark.

*Magnolia* bark extract is present in the coating, and zinc in the core of a sugar-free chewing gum pellet. The *magnolia* bark extract is preferably present in amounts ranging from 0.5 mg to 50 mg per single portion of chewing gum, and even more preferably from 1 to 5 mg per single portion. The zinc is inserted, at least partly, in microgranules containing more than 80% sorbitol and less than 2% gum arabic, as described above, and a single portion of chewing gum preferably contains 0.012 mg to 1.2 mg of zinc, even more preferably 0.05 to 0.5 mg of zinc. The zinc concentration in the microgranules containing sorbitol preferably ranges between 0.06% and 6%, even more preferably between 0.5% and 3% (percentages of the weight of the microgranule).

The microgranules can contain edible additives such as dyes, thickeners, acidifiers, sweeteners, flavours, vitamins and other mineral salts.

A single portion of chewing gum made according to the preferred form just described presents a surprising ability to reduce the volatile sulphur compounds in the air exhaled by persons with clinical halitosis, and can therefore be used to treat the symptoms of halitosis.

In fact, in consumers with a minimum VSC value of 75 ppb in the air exhaled immediately before chewing gum, a single portion of chewing gum, chewed for 10 minutes, reduces the mean concentration of volatile sulphur compounds in the exhaled air by a minimum of 40% after chewing, compared with the value before chewing.

Moreover, a single portion of chewing gum, chewed for 10 minutes by consumers with a minimum VSC value of 75 ppb in the exhaled air, reduces the mean concentration of volatile sulphur compounds in the exhaled air by at least 15% one hour after the start of chewing.

VSC is measured with the OralChroma portable gas Chromatograph© (OralChroma™, Abilit Corp., Osaka, Japan), which is readily available on the market.

Chewing gum formulations without zinc, *magnolia* or both (reference formulations A, B and C) were compared with the formulations according to the invention containing both zinc and *magnolia* extracts (formulations D, F and E). The composition of the formulations was otherwise identical. In particular, gums in pellet form were used wherein the zinc was introduced into microgranules in the core (first region), and the *magnolia* bark extract was introduced into the coating (second region). The amounts of zinc and *magnolia* bark extract are set out in table 1.

The volatile sulphur compounds were evaluated in 10 volunteers with a minimum VSC level of 75 ppb (regardless of the time of day, and without stimulating VSC production with amino acids or particular foods). The evaluation was conducted, by the method described, before chewing, immediately after chewing a single portion (10 minutes), and after one hour. Table 1 shows the % reductions in VSC compared with the starting condition. At the end of chewing, the volunteers conducted a sensory evaluation of the chewing gum.

Similarly, the ability to reduce VSC was evaluated in a preferred form of embodiment (formulation G) wherein at least 15% zinc (as a percentage of the total zinc) is inserted into microgranules containing more than 80% sorbitol and less than 2% gum arabic, as described above, and preferably, a single portion of chewing gum contains 0.012 mg to 1.2 mg of zinc, even more preferably 0.05 to 0.5 mg of zinc. The zinc carried by the microgranules is inserted as ion of a salt selected from zinc chloride, acetate, lactate, gluconate and mixtures thereof. The remainder of the zinc, below 85% (as a percentage of the total zinc) is carried by one or more of zinc chloride, acetate, lactate, gluconate and mixtures thereof inserted directly into the region containing gum base, or the core, in the case of chewing gum pellets.

The data demonstrate that chewing gum A (reference) has a certain effect of reducing oral VSC, especially after chewing, but this effect is greatly reduced after 1 h. This effect is probably due to stimulation of salivation which, together with the mechanical rubbing action on the teeth, washes away some of the bacteria that cause bad breath. The reference gum containing zinc alone improves the reduction in oral VSC, but mainly in the long term. The reference gum containing *magnolia* bark extract alone is more effective immediately after chewing, but behaves in a similar way to the gum without *magnolia* and zinc after 1 hour.

The gums with synergic combinations of zinc and *magnolia* bark extract (D, E, F and G) markedly reduce the percentage of oral VSC immediately, after 10 minutes' chewing, and after 1 h. The reduction, at both times and in all four formulations (D, E, F and G), is greater than that elicited by the gum without zinc and MBE and by the two gums B and C only containing one of the two functional ingredients, indicating a synergic effect immediately after chewing and in the longer term (see data after 1 h).

By way of further demonstration of the synergic effect of the formulations with zinc and *magnolia* according to the invention, the percentage synergic effect can be calculated. It can be considered as the percentage reduction of VSC by the gum that exceeds the sum of the VSC-reducing effects of the gums containing only one of the two functional ingredients, less the effect of the chewing gum not containing any functional ingredient. It is particularly important to subtract the effect of the plain chewing gum (Gum A in table 1) whenever the effect of a gum (whether inventive or reference) is added, similarly to the procedure used with background noise. The synergic effect is reported in table 2. Numbers higher than 0 indicate a synergic effect of the combination of zinc and vegetable extract in the inventive formulations.

TABLE 1 influence of some formulations on the VSC in the breath

| Ingredients | A reference no Zn or MBE | B reference Zn but no MBE | C reference MBE but no Zn | D invention Zn + MBE | E invention Zn + MBE | F invention Zn + MBE | G invention Zn + MBE |
| --- | --- | --- | --- | --- | --- | --- | --- |
| Core with Zn (mg/portion) | 0 | 0.1 | 0 | 1.2 | 0.1 | 0.012 | 0.3 |
| Coating with vegetable extracts (mg/portion) | 0 | 0 | 3.5 | 0.5 | 3.5 | 50 | 3 |
| % VSC after 10 min chewing. | −32 | −34 | −43 | −45 | −51 | −57 | −57 |
| % VSC after 1 h. | −7 | −22 | −5 | −35 | −28 | −27 | −44 |
| Sensory evaluation | fresh, pleasant mint flavour | similar to A | similar to A | freshness similar to A, astringent flavour | similar to A | freshness similar to A, bitter flavour | similar to A |

TABLE 2

% synergic effect

| | D invention Zn + MBE | E invention Zn + MBE | F invention Zn + MBE | G invention Zn + MBE |
| --- | --- | --- | --- | --- |
| % synergy after 10 min | 0 | 46 | 92 | 92 |
| % synergy after 1 h | 115 | 62 | 54 | 185 |

Doses higher than those used in formulations D and F would produce unpleasant alterations (astringency, bitterness) in the flavour of the formulation, which could reduce compliance with treatment designed to reduce the symptoms of halitosis.

It is particularly advantageous for the fully water-soluble region without gum base to consist of a coating consisting of over 70% maltitol by dry weight, and preferably over 85% by dry weight (percentages of total coating). In an alternative, but equally advantageous form of embodiment, maltitol is replaced by a mixture of glucopyranosyl-mannitol and glucopyranosyl-sorbitol or a mixture of xylitol and mannitol.

The MBE released from the chewing gum thus formulated in 10 minutes' chewing ranges between 50% and 80% (of the total MBE).

It is advantageous to add zinc, in an amount ranging between 0.0005% and 0.05% of the chewing gum, through microgranules containing more than 80% sorbitol, less than 2% gum arabic and more than 1% zinc salt (percentages of the total microgranule), added to the zone containing gum base. The zinc released from the chewing gum thus formulated in 10 minutes' chewing ranges between 50% and 80% (of the total zinc).

The chewing gum wherein at least 15% zinc (as a percentage of the total zinc) is inserted in microgranules, which are inserted directly in the region containing gum base, as ion of a salt selected from zinc chloride, acetate, lactate, gluconate and mixtures thereof, and the remaining amount of zinc is carried by one or more of zinc chloride, acetate, lactate, gluconate and mixtures thereof inserted directly in the region containing gum base, also possesses a similar release over time.

The embodiment illustrated therefore allows the simultaneous release of comparable amounts of MBE and Zn, which can perform the synergic action in the oral cavity.

The addition of flavours containing spilanthol or pellitorine promotes the release of active agents, and is particularly indicated in combination with mint flavours.

The invention also relates to a method of treating the symptoms of halitosis in humans, comprising the following steps:

1) placing in the oral cavity of a patient with halitosis a piece of chewing gum consisting of at least:

a) a first region with gum base having a zinc content ranging from 0.0005% to 0.05% of the chewing gum, provided by microgranules, said microgranules containing more than 80% sorbitol, less than 2% gum arabic and more than 1% zinc salt (percentages of total microgranule);

b) a second region, without gum base, consisting of a fully water-soluble coating, characterized in that it contains more than 75% maltitol, glucopyranosyl-sorbitol and glucopyranosyl-mannitol mixture, or xylitol and mannitol mixture, and contains *magnolia* bark extract ranging from 0.02% to 2% of the chewing gum;

2) chewing of said one piece of chewing gum for 10 minutes, said gum being able to release into the oral cavity, in 10 minutes' chewing, between 40% and 80% of its *magnolia* bark extract content (as a percentage of the total extract) and between 50% and 80% (as a percentage of the total zinc), so that said ingredients perform a synergic action against the symptoms of halitosis.

An example of a microgranule containing zinc, a microgranule according to the invention, a comparative example and an efficacy evaluation test are set out below.

Example 1: Composition of Microgranules Used in the Gum According to the Invention

| Ingredients of microgranule | Example 1 % |
|---|---|
| Sorbitol | 85.00 |
| Xylitol | 8.00 |
| Acesulfame K | 1.00 |
| Flavours | 0.80 |
| Green colouring | 0.20 |
| Gum arabic | 0.50 |
| Zinc lactate | 3.10 |
| Water | 1.40 |
| Total microgranule | 100 |

Tables 3 below illustrates the chewing gum compositions according to the invention (example 3) and a reference compositions (example 2). Said gums take the form of filled pellets, consisting of three separate regions: filling (region without gum base), core (region with gum base), and coating (region without gum base).

The percentages are expressed in relation to the total of the single portion. The values in mg refer to a portion weighing 2.2 g which, in the example, corresponds to a single piece.

TABLE 3

| | Reference example 2 | | Example 3 | |
|---|---|---|---|---|
| Ingredients | % | mg per piece | % | mg per piece |
| Filling (region without gum base, fully water-soluble) | | | | |
| Maltitol syrup | 6.700 | 147.400 | 6.700 | 147.400 |
| Acesulfame K | 0.001 | 0.022 | 0.001 | 0.022 |
| Sucralose | 0.001 | 0.022 | 0.001 | 0.022 |
| Flavours | 0.057 | 1.254 | 0.057 | 1.254 |
| Blue colouring | 0.001 | 0.022 | 0.001 | 0.022 |
| Emulsifier | 0.008 | 0.176 | 0.008 | 0.176 |
| Glycerol | 0.100 | 2.200 | 0.100 | 2.200 |
| Thickener | 0.002 | 0.044 | 0.002 | 0.044 |
| Water | 0.130 | 2.860 | 0.130 | 2.860 |
| Total filling | 7.000 | 154.000 | 7.000 | 154.000 |
| Core (region with gum base) | | | | |
| Gum base | 22.700 | 499.400 | 22.700 | 499.400 |
| Microgranules, example 1 (of which Zn) | 0.000 | 0.000 | 0.600 (0.005) | 13.200 (0.11) |
| Aspartame | 0.050 | 1.100 | 0.050 | 1.100 |
| Acesulfame | 0.050 | 1.100 | 0.050 | 1.100 |
| Sucralose | 0.030 | 0.660 | 0.030 | 0.660 |
| Encapsulated aspartame | 1.300 | 28.600 | 1.300 | 28.600 |
| Maltitol syrup | 1.870 | 41.140 | 1.870 | 41.140 |
| Mannitol | 5.800 | 127.600 | 5.800 | 127.600 |
| Powdered maltitol | 18.000 | 396.000 | 18.000 | 396.000 |
| Xylitol | 3.500 | 77.000 | 3.500 | 77.000 |
| Flavours | 2.000 | 44.000 | 2.000 | 44.000 |
| Sorbitol | 7.700 | 169.400 | 7.100 | 156.200 |
| Total core | 63.000 | 1386.000 | 63.000 | 1386.000 |
| Coating (region without gum base, fully water-soluble) | | | | |
| Maltitol | 27.5 | 605.000 | 27.35 | 601.700 |
| Gelatin | 0.07 | 1.540 | 0.07 | 1.540 |
| Gum arabic | 1.77 | 38.940 | 1.77 | 38.940 |
| White colouring | 0.47 | 10.340 | 0.47 | 10.340 |
| Flavours | 0.06 | 1.320 | 0.06 | 1.320 |
| Aspartame | 0.05 | 1.100 | 0.05 | 1.100 |

TABLE 3-continued

|  | Reference example 2 | | Example 3 | |
|---|---|---|---|---|
| Ingredients | % | mg per piece | % | mg per piece |
| Acesulfame | 0.05 | 1.100 | 0.05 | 1.100 |
| Magnolia bark extract | 0.00 | 0.000 | 0.15 | 3.300 |
| Carnauba wax | 0.03 | 0.660 | 0.03 | 0.660 |
| Total coating | 30 | 660.000 | 30 | 660 |
| Total filling/core/coating | 100.000 | 2200.000 | 100.000 | 2200.000 |

Activity Test for Treatment of Symptoms of Halitosis

A test was conducted with OralChroma on the gum according to the invention (example 3) compared with the reference gum (example 2), to measure the oral VSC of volunteers having a minimum oral VSC value of 75 ppb. A product available on the market was tested, consisting of sugar-free corrugated tablets with herbal extracts (0.36% green coffee beans and 0.36% burdock). The methodology used to measure the VSC is as previously described.

The results are summarized in table 4 below.

TABLE 4

| | % reduction in oral VSC concentration compared with concentration before chewing | | |
|---|---|---|---|
| time | gum according to the invention (Example 3) | control gum not containing Zn or MBE (Example 2) | tablet on the market |
| after 10 min chewing | 50.9 | 31.2 | 23.9 |
| after 1 h | 27.6 | 6.9 | 5.1 |
| after 2 h | 13.6 | 2.3 | 4.9 |

The gum according to the invention is clearly able to reduce the oral concentration of VSC to a greater extent than (i) gum not containing any functional ingredients and (ii) the product on the market, both immediately after chewing and after one or two hours.

The invention claimed is:

1. A method of treating halitosis symptoms in a patient in need thereof, said method comprising:
   placing in oral cavity of the patient with halitosis a single portion of chewing gum comprising at least one first region with gum base and at least a second fully water-soluble region without gum base, said chewing gum characterized by the presence of a synergistic combination of:
   a) from 0.5 mg to 50 mg of *magnolia* bark extract, and
   b) from 0.012 mg to 1.2 mg of zinc ions contained in fully water-soluble microgranules,
   wherein the first region comprises the zinc ions contained in fully water-soluble microgranules, and the second region comprises the *magnolia* bark extract; and chewing said chewing gum.

2. The method according to claim 1, wherein the *magnolia* bark extract comprises magnolol and honokiol, in a concentration higher than 80% by weight of the extract.

3. The method according to claim 1, wherein said water-soluble microgranules comprise one or more polyalcohols, hydrocolloids, flavours, dyes, sweeting agents and excipients, alone or in mixture thereof, said microgranules having an average particle-size distribution lower than 1000 μm.

4. The method according to claim 1, wherein the zinc ion content in the chewing gum ranges from 0.0005% to 0.05% by weight and the *magnolia* bark extract content in the chewing gum ranges from 0.02% to 2% by weight.

5. The method according to claim 1, wherein the single portion chewed for 10 minutes by a consumer with a minimum volatile sulfur compounds (VSC) value in the oral air of 75 ppb is capable of reducing, immediately after chewing, the average concentration of VSC in the oral air by at least 40% compared to the value before chewing.

6. The method according to claim 1, wherein the single portion chewed for 10 minutes by a consumer with a minimum volatile sulfur compounds (VSC) value in the oral air of 75 ppb is capable of reducing, one hour after starting chewing, the average concentration of VSC in the oral air by at least 15% compared to the value before chewing.

7. The method according to claim 1, wherein the zinc ion is present as a salt selected from the group consisting of zinc chloride, acetate, lactate, gluconate, butyrate, glycerate, glycolate, formate, picolinate, propionate, salicylate, tartrate, sulfate, ascorbate, bisglycinate, lysinate, malate, mono-L-methionine sulfate, pidolate and mixtures thereof.

8. The method according to claim 4, wherein an additional zinc salt is present in the chewing gum, the additional zinc salt is selected from the group consisting of zinc oleate, stearate, citrate, phosphate, carbonate, borate, oxalate, aspartate, oxide and mixtures thereof.

9. The method according to claim 8, wherein the single portion of chewing gum contains said additional zinc salt in such amounts as to supply 0.1 to 10 mg of zinc.

10. The method according to claim 1, wherein said first region with gum base forms a core and said second fully water-soluble region, without gum base, forms a coating layer that at least partially coats the first region.

11. The method according to claim 10 wherein more than 70% by dry weight of the coating layer consists of maltitol or a mixture of glucopyranosyl-mannitol and glucopyranosyl-sorbitol.

12. The method according to claim 10 wherein a filling is also present inside said first region.

13. The method according to claim 12 wherein said filling contains one or more of polyalcohols, excipients, emulsifiers, vitamins, mineral salts, *magnolia* bark extracts, dyes, acidifiers and flavours.

14. The method according to claim 1 wherein said first region and said second region are arranged in overlapping, alternating layers.

15. The method according to claim 1, wherein the chewing gum further comprising at least one flavour selected from the group consisting of the genera *Mentha, Citrus, Spilanthes*, menthol, artificial flavours, natural flavours, and combinations thereof, wherein said at least one flavour act as cooling and salivating agents.

* * * * *